United States Patent
Owens

(10) Patent No.: US 7,849,747 B2
(45) Date of Patent: Dec. 14, 2010

(54) FLAW DETECTION IN EXHAUST SYSTEM CERAMIC MONOLITHS

(75) Inventor: Christopher Simon Owens, Melvindale, MI (US)

(73) Assignee: Umicore AG & Co. KG, Hanau-Wolfgang (DE)

( * ) Notice: Subject to any disclaimer, the term of this patent is extended or adjusted under 35 U.S.C. 154(b) by 322 days.

(21) Appl. No.: 12/044,147

(22) Filed: Mar. 7, 2008

(65) Prior Publication Data

US 2009/0223293 A1  Sep. 10, 2009

(51) Int. Cl.
  *G01N 29/06* (2006.01)
  *G01N 29/22* (2006.01)
(52) U.S. Cl. .............................. 73/598; 73/620; 73/629
(58) Field of Classification Search ................... 73/598, 73/600, 620, 629
  See application file for complete search history.

(56) References Cited

U.S. PATENT DOCUMENTS

| | | | |
|---|---|---|---|
| 4,557,773 A | 12/1985 | Bonzo | |
| 4,631,269 A | 12/1986 | Lachman et al. | |
| 4,752,516 A | 6/1988 | Montierth | |
| 5,743,087 A | 4/1998 | Zahn et al. | |
| 5,964,694 A | 10/1999 | Siess et al. | |
| 6,439,054 B1 | 8/2002 | Gore et al. | |
| 6,890,616 B2 | 5/2005 | Suwabe et al. | |
| 6,945,111 B2 * | 9/2005 | Georgeson | 73/600 |
| 7,614,304 B2 * | 11/2009 | Gunasekaran et al. | 73/598 |
| 2005/0247131 A1 | 11/2005 | Breuer | |
| 2006/0137525 A1 | 6/2006 | Rae et al. | |
| 2007/0144260 A1 * | 6/2007 | Fei et al. | 73/596 |
| 2007/0144263 A1 * | 6/2007 | Fei et al. | 73/644 |
| 2007/0266547 A1 * | 11/2007 | Shi | 29/594 |
| 2007/0266789 A1 * | 11/2007 | Hampton et al. | 73/596 |
| 2009/0120189 A1 * | 5/2009 | Fei et al. | 73/596 |

FOREIGN PATENT DOCUMENTS

JP   2006106011 A  *  4/2006

* cited by examiner

*Primary Examiner*—Daniel S Larkin
*Assistant Examiner*—Rose M Miller
(74) *Attorney, Agent, or Firm*—Brooks Kushman P.C.

(57) ABSTRACT

Ultrasonic detection of flaws in ceramic monoliths such as are commonly used in diesel particulate filters is made possible by beaming ultrasound into the monolith from an inlet or outlet face thereof and analyzing the reflected ultrasound from the same face. The monolith is preferably rotated during the scan, or the scan may be repeated from several rotational positions relative to the face of the monolith. Even small flaws which are hard to detect may be identified.

41 Claims, 3 Drawing Sheets

FLAW DETECTION IN EXHAUST SYSTEM CERAMIC MONOLITHS

BACKGROUND OF THE INVENTION

1. Field of the Invention

The present invention pertains to a method for inspection of ceramic monoliths for use in exhaust systems.

2. Description of the Related Art

Ceramic monoliths are widely used in exhaust system components as catalytic elements or as particulate traps. In common applications, one or a plurality of monoliths, generally in honeycomb form, are impregnated and/or coated with catalytic materials, then packaged into a metal "can".

The manufacture of such monoliths include numerous steps such as forming by casting or extrusion methods, drying, sintering, impregnating, wash-coating, firing, etc. Damage to the monolith may occur in each of these steps. While some damage is external and immediately visible, internal damage is not, and if gone unnoticed, may result in production of a defective exhaust catalyst element, or one which may later fail. In monoliths with internal damage, the hot/cold cycles which the monoliths will experience result in deterioration of the monolith. Internal damage in components such as particulate filters can allow particle laden exhaust gas to flow through the filter without any filtering. Thus, it would be desirable to be able to determine whether ceramic monoliths for exhaust systems have any internal damage. It would further be desirable to be able to detect such damage at multiple stages during the manufacturing process, for example both prior to and after catalyst deposition.

Ultrasonic imaging has been used in numerous fields to determine product shape, and in some cases, internal damage. An example is the measurement of impact damage on quasi-iotropic laminates for aerospace applications (so-called "c-scan"). A further example is disclosed in U.S. Pat. No. 6,439,054, where ultrasonic imaging is employed to test homogeneity of sputtering target materials. Both these methods, however, require application of ultrasonic energy in a water bath, which is not satisfactory for use with porous and water absorbent ceramic materials.

Corning U.S. Pat. No. 4,557,773 ("Corning") discloses the use of ultrasound to determine the location of alternating open and closed passageways in a monolithic diesel particulate filter ("DPF") after a ceramic end cap has been applied by directing ultrasound into the monolith and detecting transmitted ultrasound at the opposite face, while Corning U.S. Pat. No. 4,752,516 discloses the use of ultrasound to assist in the introduction of polymer into cells to form a mask. However, neither of these patents discusses detection of flaws. U.S. published application 2005/0247131 and U.S. Pat. No. 5,964,694 disclose the use of ultrasound to determine the degree of plugging of DPFs. However, no scan is performed, only a test based by changes in reflected ultrasonic energy.

In U.S. published application 2006/0137525, Corning, Inc. a pioneer in monolith production and testing, discloses several methods of testing plugged honeycomb structures such as are commonly used for diesel particulate filters. However, despite the availability of ultrasonic methods for use in other areas of technology, use of ultrasonic testing is not disclosed. Rather, tests such as monitoring the pass through of graphite powder, the through-flow of soot-containing gases, and use of temperature sensitive LCP films while blowing cool air through the monolith, have all been used. In the '525 application, ultrasonic energy is used in an ultrasonic humidifier to produce a vapor which flows through the honeycomb and is then later is detected downstream from the honeycomb.

One reason that ultrasound has not been used for testing ceramic monoliths for the presence of flaws may have to do with their structure, which is generally a multiplicity of parallel passages (cells) with porous ceramic walls. Aiming ultrasound through these cells and detecting the transmitted sound at the opposite face of the monolith may detect plugged or collapsed cells, but may not always detect flaws such as holes in the cell walls, cracks, etc. Aiming ultrasound into the cell and observing the reflected signal would be expected to be associated with such a variety and number of internal reflections/re-reflections that such a technique would not be considered viable.

SUMMARY OF THE INVENTION

It has now been surprisingly discovered that flaws in porous ceramic monoliths, for example those suitable for use in exhaust systems of internal combustion engines, may be identified by an ultrasonic scanning technique wherein an ultrasonic transducer or transducer array directs acoustic energy into the monolith from one end, and reflected ultrasonic energy is received at the same end of the monolith and analyzed for signals indicative of flaws. Even relatively small and hard-to-detect flaws may be located, despite the multiple reflections characteristic of cellular materials.

DETAILED DESCRIPTION OF THE PREFERRED EMBODIMENT(S)

Figure 1:
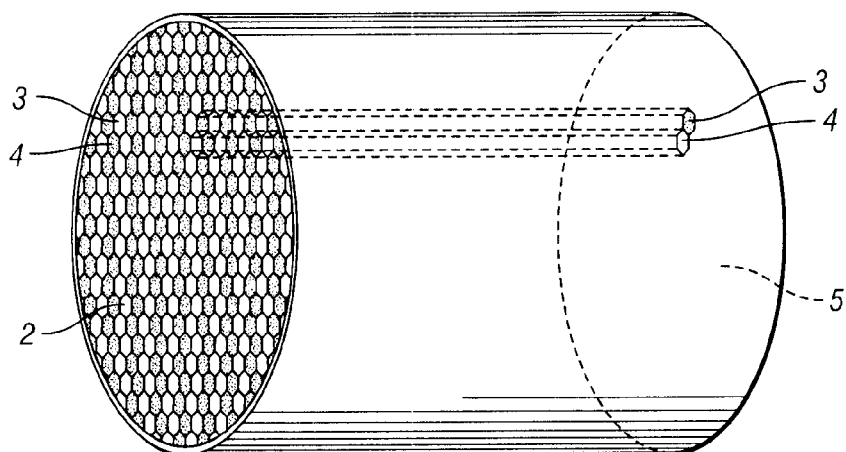
FIG. 1 illustrates a prior art diesel particulate filter (DPF) monolith.

The ceramic monoliths which are analyzed may be any which are useful in conditioning the exhaust gases of internal combustion engines. Such monoliths are described in numerous patents and publications, for example U.S. Pat. Nos. 4,631,269, 5,743,087, and 6,890,616, all incorporated herein by reference. While infrequently such monoliths may constitute an open celled ceramic foam, most commonly the monoliths are "honeycomb" materials containing a regular geometric array of parallel passageways or "cells. The cell cross-section may be of any geometrical shape, for example triangular, square, hexagonal, circular, etc., but is most often of square cross-section. A typical DPF monolith is shown in FIG. 1, in perspective. The monolith 1 has a first, or front face 2 which contains a regular array of cells 3, 4. Alternating cells are plugged, such that for example, cell 3 is open and cell 4 is closed. On the second, or rear face 5, the cells from the front face reach the rear face. However, the cells which were open on the front face, e.g. 3, are closed on the rear face, and the cells which were closed on the front face, e.g. 4, are open on the rear face. The result is that there is no open flow path from the front face of the monolith to the rear face. Thus, gas applied to the front face, to exit at the rear face, must pass through the porous ceramic wall which makes up the walls of the cells. For example, gas entering open cell 3 must pass through the wall of this cell into adjoining cells which, though closed on the front face of the monolith, are open at the rear face. The porosity of the ceramic and the large surface area of the cells allows for considerable flow of gas, without unduly increasing exhaust system back pressure. However, particulate matter such as soot is trapped on the cell walls. This soot is removed by combusting it, generally under temporary high temperature conditions. The temperature needed for combustion may be decreased by adding a combustion-promoting catalyst to the monolith, for example Pt. The temperature generated by burning the soot can be very high, and as a result, considerable thermal stress is placed on the monolith. Small flaws can potentially become large flaws during temperature cycling. Defects in the walls between open and closed cells can allow particulate matter to pass through the filter unimpeded.

Exhaust systems also employ a variety of monoliths to reduce non-particulate engine emissions such as CO, HC (hydrocarbons) and $NO_x$. These monoliths have at least one and sometimes a plurality of catalysts deposited on the monolith. One catalyst might be for the purpose of removing CO, for example, while another might be used to reduce $NO_x$. The same monolith may have a plurality of catalytic systems uniformly co-deposited, or may have a front end containing one catalytic system and a second end having another system. Many variations are possible. Exhaust systems quite commonly have several monoliths in series, performing the same or different functions.

As with DPFs, these emission-reducing monoliths are also subject to temperature cycling. This temperature cycling is especially severe for monoliths located close to the exhaust manifold. Thus, even though the predominant flow is not through the cell walls (all cells in such monoliths are usually open on both ends), failure due to flaw propagation is still a possibility.

The test method of the subject invention is for the purpose of detecting flaws in the various monoliths prior to canning (placing the monolith within its metal exhaust component shell) or following insertion into the can but prior to closing the can. The method is effective to locate even relatively small flaws, and may be used with monoliths of greatly divergent cell sizes, widths, and lengths. The test method involves closely coupling an ultrasonic transducer to either face of the monolith, for example the front face, generating ultrasonic signals, preferably of the pulse/echo and/or phased array type, and preferably moving either the transducer or monolith to provide relative movement therebetween, such that the scan produced takes in the entire width of the monolith. Alternatively, a larger transducer array might be used to cover the entire width of the filter element, or a plurality of separate transducers may be used.

By the term "transducer" is meant a device which generates and detects ultrasonic energy. A transducer may have but a single ultrasonic generator, or may have a multiplicity of such generators. The detectors may be the same or different from the ultrasonic generators, and may be located adjacent or spaced apart from the ultrasonic generators. Quite frequently, the generators are present in a regular array, for example a 2×2, 4×4, 4×6, 16×16, or other array. Linear arrays, for example 1×16 arrays, circular arrays, and arrays of numerous other geometric shapes are known in the art of ultrasound applications. The transducer directs ultrasound into the monolith, and reflected ultrasound (echo) is detected by the detector(s). The detected reflections generate an electrical signal which is directed, either in analog or digital form, to an appropriate analyzer. As transducers are often arrays of individual generators/receivers, the term "array" as used herein is synonymous with "transducer."

By "close coupling" and similar terms is meant acoustical coupling such that an ultrasonic signal of appropriate strength may be applied to the monolith and a return signal (reflected signal) of analyzable strength is obtained. In general, for example, simply spacing the transducer apart from the face of the monolith will not provide close coupling, nor will simple physical contact. Close coupling can be achieved by several methods, and additional methods will be apparent to one skilled in the art of ultrasonic non-destructive testing. In the present invention, close coupling cannot be achievable by immersion in a liquid, which is commonly performed with numerous test methods, because this would require subsequent thorough drying of the monolith, an extra process step. Furthermore, any soluble components, for example ionic catalysts or water soluble catalyst precursors will be leached out.

Close coupling is preferably performed with the aid of a gel-like or grease-like substance or a viscous liquid, an elastomeric membrane, or both. Most preferably, an elastomeric sheet material is applied over the face of the monolith, preferably over the entire face. The transducer is then pressed against this elastomeric sheet. A gel, grease, or viscous liquid may be applied between the transducer and the elastomeric sheet. The gel further facilitates close coupling, and may also serve a lubricant function when relative movement between the transducer and monolith face is desired without lifting the transducer from contact with the sheet. A preferred elastomeric sheet material is a polyurethane elastomer sheet having a thickness of 1/32 inch (0.8 mm) and a Shore A hardness of 60, available in sheets from Panametrics as part number NPD-665-3101. However, other elastomeric materials of a variety of thicknesses and hardnesses may be used as well. Such materials may be tested easily for their suitability by simply testing a monolith employing the material. A standard test monolith may be retained for this purpose. A key parameter in testing will be the strength of the reflected signal at a given ultrasound power output.

In principle, the transducer may be equipped with an elastomer on its surface, often with gel material between the elastomer and the transducer per se. However, this method is less preferred, since relative movement between the transducer and monolith is rendered more difficult. The monolith face is seldom so smooth that sliding an elastomer-faced transducer over the face is easily accomplished. When such an embodiment is used, it is preferred that the elastomer have a thin coating of a lubricious polymer such as PTFE, polyethylene, polypropylene, etc. The same coatings may also be applied, in particular, to the transducer-side of the elastomeric sheet material which is applied preferably over the entire face of the monolith. This coating is desirably thin, and tailored to the elastomer sheet materials such that signal reflection at the elastomer/coating interface is minimized.

In principle, gel may also be applied to the monolith. However in most cases, this gel will have to be removed, thus again requiring an extra process step. Thus, this type of coupling is not desired. Gels which are hydrocarbon based and which can be left on the monolith, being removed by an initial burnout, are preferred in such instances.

The transducer and associated equipment should be capable of scanning at least one half the depth (length) of the monolith. In such cases, it may be necessary to scan from both ends of the monolith in order that the entire depth be scanned. However, it is much more preferable that the scan depth be such that the entire depth of the monolith can be scanned from one side. By "depth" is meant a length parallel to the general gas flow direction. In honeycomb monoliths, this direction is parallel to the cell length.

It is also preferable that the transducer array be large enough such that the entire width (diameter) of the monolith can be scanned. In this case, no relative movement between the transducer and the monolith may be necessary, or only a number of alternative transducer positions may be required. However, for maximum detection of flaws, some relative movement may be desirable, as under these conditions, a moving scan will be created which may assist in quantifying defects.

The transducer output is preferably from an array of individual transducers which form a phased array. In such arrays, the output, due to principles of interference, generally assumes the shape of a cone, the width of the cone increasing in a direction away from the transducer. This cone may be substantially two dimensional, i.e. a flat cone, produced by a linear transducer array, or may be three dimensional. The particular array used, and the shape of its ultrasound "envelope" is not critical, so long as flaws can suitably be detected. Transducers are preferably tested by retaining one or more monoliths with known flaws and determining whether or not with a given transducer, the flaws can be detected.

The "cone" output by the transducer is preferably directed downwards into the core of the monolith parallel with the dissection of the cells, i.e. in the direction gas flow would take if unobstructed. The cone may also be directed at an angle to the monolith. In phased array transducers, the direction in which the cone is oriented may also be altered by exciting individual transducer elements in a time-staggered fashion. In this mode, the alternating frequency applied to successive transducer elements is partially delayed such that ultrasonic radiation is not in phase. Thus, the cone may be "steered" by this method. Steering may take place along only a single direction, or multiple directions at once. For example with rectangular or square arrays of emitting elements, the cone may be caused to sweep a circular path. With a suitably large array, whether linear or two-dimensional, this steerable sweep may take the place of moving the transducer to varying positions along the face of the monolith. Alternatively, a plurality of transducer arrays, preferably of different emission frequencies or whose emission is staggered in time may be used. In the latter case, it may be appropriate to employ phase lock signal filtering to isolate ultrasound reflection from respective transducers to increase signal accuracy.

Figure 2A:
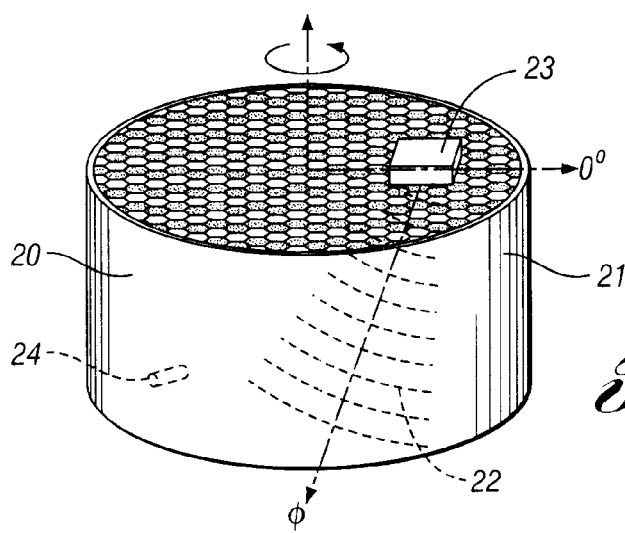
FIGS. 2a and 2b illustrate one embodiment of ultrasonic flow detection employing angular transducer(s) positioned at different positions around the face of a monolith.

In a further preferred embodiment, the transducer emits ultrasound at an angle to the face of the monolith. The angle with the monolith face is generally in the range of 10° to 35°, more preferably 15-20°. These angles are measured from a normal to the face. When such a transducer is placed near the edge of one face of the monolith, as shown in FIG. 2a two areas of shadow, 20, 21 form because the ultrasound 22 emitted from the transducer 23 located at one spot (0° relative to a circular face of the monolith comprising 360°) does not reach these areas. Rotating the transducer by 180° causes these "shadow" areas to be scanned as well. This is why relative rotation is desirable. Alternatively, rather than a repositioning or a rotation, two equivalent arrays may be located 180° apart, with any one array active at a time. While it is theoretically possible to pulse both arrays simultaneously with somewhat different frequencies and with the use of synchronous filters, "phase-lock loop" filters, etc., this additional complexity is not desirable.

As shown in FIG. 2a, a transducer 23 emits an angled cone of ultrasound 22 into the monolith 1 (FIG. 1). The cone makes an angle φ with respect to an axis orthogonal to the monolith face 2 (FIG. 1). If the monolith is radically symmetrical as most are, it may be rotated around its axis (as shown by the arrow extending from the monolith face), or the monolith may be stationary and the transducer moved across the face, around the face, or both. A cylindrical defect in the monolith is shown at 24. The scans obtained will show an irregularity at the location of this defect, allowing the monolith to be removed from production for inspection, further processing to repair the damage, if possible, or scrapping.

Figure 2B:
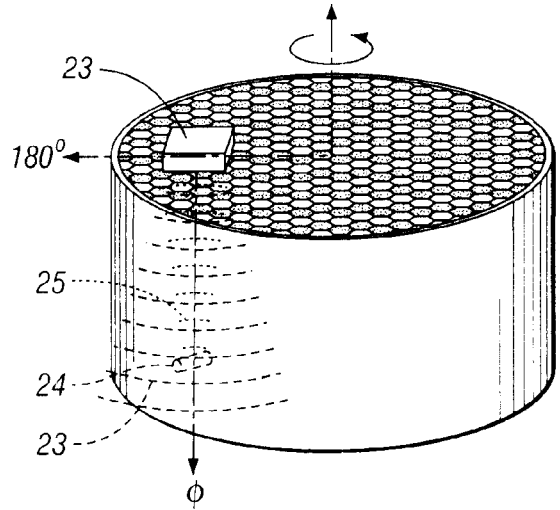

FIG. 2b is similar to FIG. 2a, but the ultrasound propagation direction is perpendicular to the face of the monolith (φ=0). Also shown is the ultrasound reflected (25) from the defect 24.

Suitable ultrasonic transducers and transducer arrays are available commercially as is signal processing equipment also. Systems may be customized if desired, and a great deal of signal processing and refinement can be performed by use of computer processing. A particularly suitable transducer is available from Omniscan, Waltham, Mass. as transducer IC16-A4. This transducer contains 16 individual ultrasonic generators operating at a nominal 1.5 MHZ, although the frequency can be varied considerably. Preferably, the signal frequency is from 0.5 MHZ to 2.5 MHZ, more preferably 0.5 MHZ to 2 MHZ, and most preferably 1.0 MHZ to 1.8 MHZ. The signal from this transducer may be analyzed by any signal analyzer. A preferred analyzer is an Omniscan MX PA. However, if implemented in a manufacturing setting, it is likely that a custom analyzer and display unit may be utilized.

Each transducer/analyzer combination may have its own unique set of operating parameters. However, one skilled in the art can easily determine, based on experience or with the aid of product manuals, which parameters are the most important. With an Omniscan™ analyzer, the most important parameters are establishing the time-corrected gain settings (TCG), a curve manually created when the focal depth of the transducer is known and the depth of scan into the monolith is established, and which assists in controlling the focus objective within the monolith; the focal depth, which may be adjusted, for example by altering the phase relationship between individual transducers; the material sound velocity, which is obtainable from standard references or manufacturers literature; and the decibel range, which determines the strength of the emitted wave and therefore also the signal strength of the reflected ultrasound.

Once all the parameters are set, scanning of the filter begins. It is preferred that rather than a single type of scan, that a plurality of scan types, preferably three scan types be made simultaneously, for example, A, B, and S scans. By using a multiplicity of scan types, one scan type can serve as an aid or check to interpreting the results of another scan type.

As an example employing a 10.5 inch diameter×12 inch depth DPF or CDPF, the settings employed are as follows:

| | |
|---|---|
| Beam Delay | 9.285 us |
| Start (Half Path) | −0.002 in |
| Range (Half Path) | 21.433 in |
| PRF | 16 |
| Type | PA |
| Averaging Factor | 1 |
| Scale Type | Compression |
| Scale Factor | 74 |
| Video Filter | On |
| Pretrig | 0.00 μs |
| Rectification | FW |
| Band Pass Filter | 1 MHZ (.4-1.7 MHZ) |
| Voltage | 80 V |
| Gain | 40.00 dB |
| Mode | PE (Pulse Echo) |
| Wave Type | User Defined |
| Sound Velocity | 0.128 in/μs |
| Pulse Width | 332.50 ns |
| Scan Offset | 0.000 in |
| Index Offset | 0.000 in |

-continued

| | |
|---|---|
| Skew | 90.0° |

The settings will also include programming the gate. These settings are 10.5"×12" filter are to be set accordingly.

| Gate | Start | Width | Threshold | Synchro |
|---|---|---|---|---|
| I | 10.000 in | 5.000 in | 40.00% | Pulse |
| A | 3.00 in | 3.000 in | 20.00% | Pulse |
| B | 6.00 in | 4.000 in | 13.00% | Pulse |

Another parameter to configure is the TCG curve (time-corrected gain curve). The settings are as follows.

| TGC Point Number | Position (half path) | Gain |
|---|---|---|
| 1 | 0.000 in | 0.0 dB |
| 2 | 0.064 in | 2.0 dB |
| 3 | 3.628 in | 3.0 dB |
| 4 | 5.692 in | 5.0 dB |
| 5 | 7.756 in | 8.0 dB |
| 6 | 10.320 in | 12.0 dB |
| 7 | 11.884 in | 16.0 dB |
| 8 | 12.662 in | 7.0 dB |
| 9 | 14.076 in | 0.0 dB |

Additional parameters that will require modifications are grouped within the scan area parameters. All these settings well known to ultrasound technicians and may be modified in the following manner.

| | |
|---|---|
| Scan Start | 0.000 in |
| Scan Length | 15.748 in |
| Scan Resolution | 0.039 in |
| Index Start | 0.000 in |
| Index Length | 0.039 in |
| Index Resolution | 0.039 in |
| Synchro | Clock |
| Max Scan Speed | N/A |

The calculator settings should be set in the following manner.

| | |
|---|---|
| Used Element Qty | 16 |
| First Element | 1 |
| Last Element | 16 |
| Resolution | 1 |
| Wave Type | User Defined |
| Material Velocity | 0.128 in/μs |
| Start Angle | −45.0° |
| Angle Resolution | 1.0° |
| Focus Depth | 12.000 in |
| Scan Type | Sectorial |

After defining the settings, the following scan types should be implemented: A-B-S. These scan types clearly define signal response to characterize the flaw within a filter from a severity and depth perspective. The three scans will provide the user with 3 separate images from one sweep scan. The A scan provides a view of a single wave across the DPF/CDPF. The S scan provides a sectorial view as it is emitting from the transducer, this signal can be set-up to have limitations and warnings by using the gate settings. The S scan can be a single point reference or can be used to analyze in a sweeping mode. This scan can be analyzed from a single point or monitored with the gate settings to qualify or disqualify the observations from the A scan. The B scan will provide a moving image that enables a user to capture the image from a sweeping scan (while moving the transducer slowly across the face of the monolith). All of these views/scans are used to help characterize a flaw in the monolith.

Figure 3A:
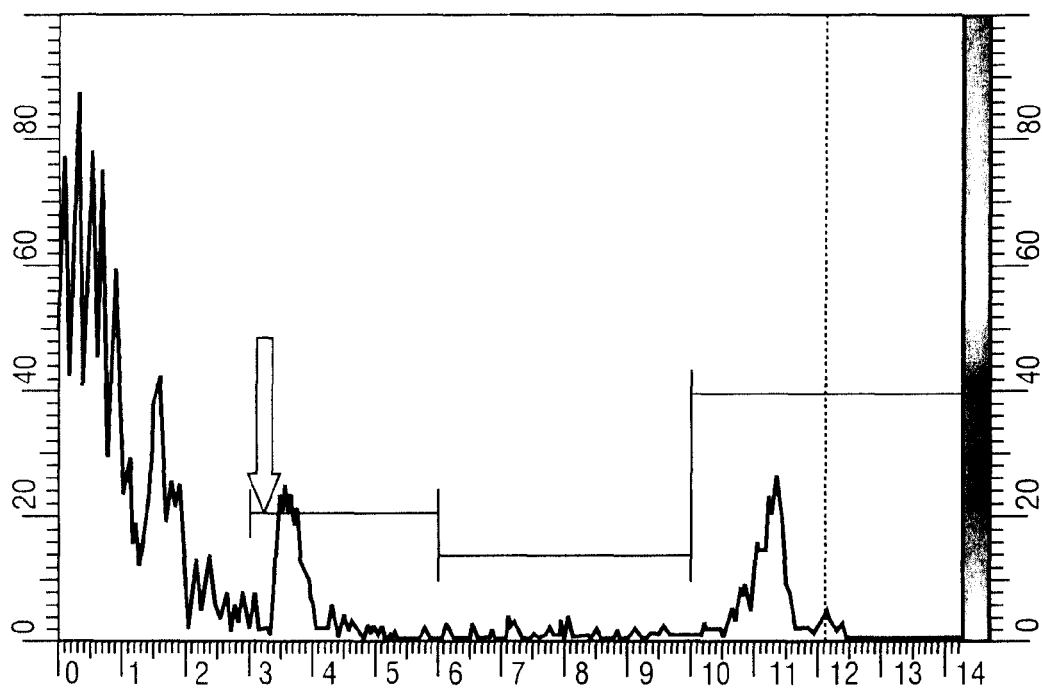
FIGS. 3a, 3b, and 3c are A, B, and S scans of a monolith purposefully damaged with a difficult-to-detect flaw showing the presence of the flaw.
Figure 3B:
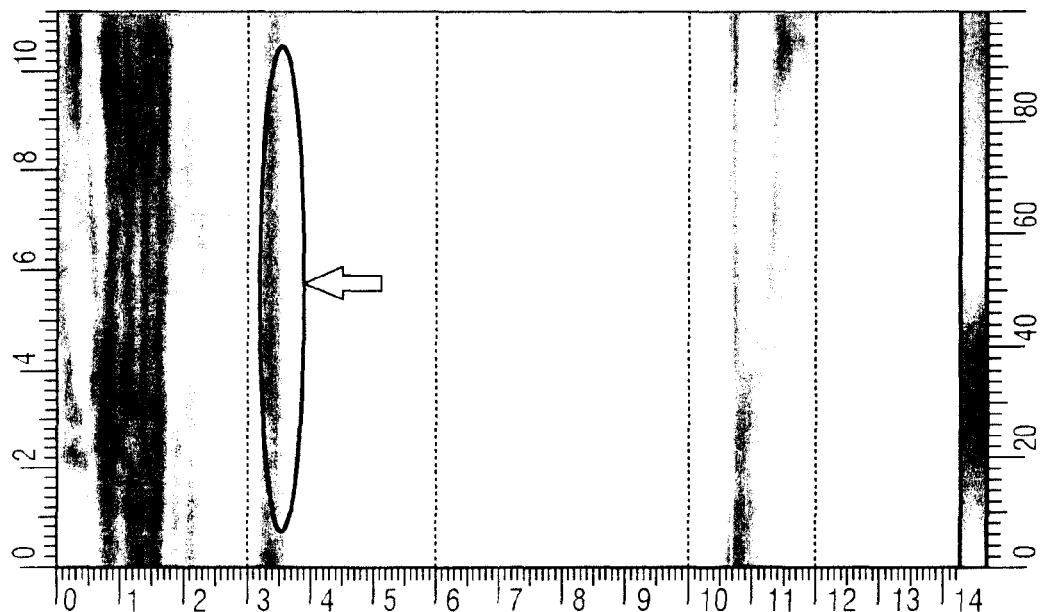
Figure 3C:
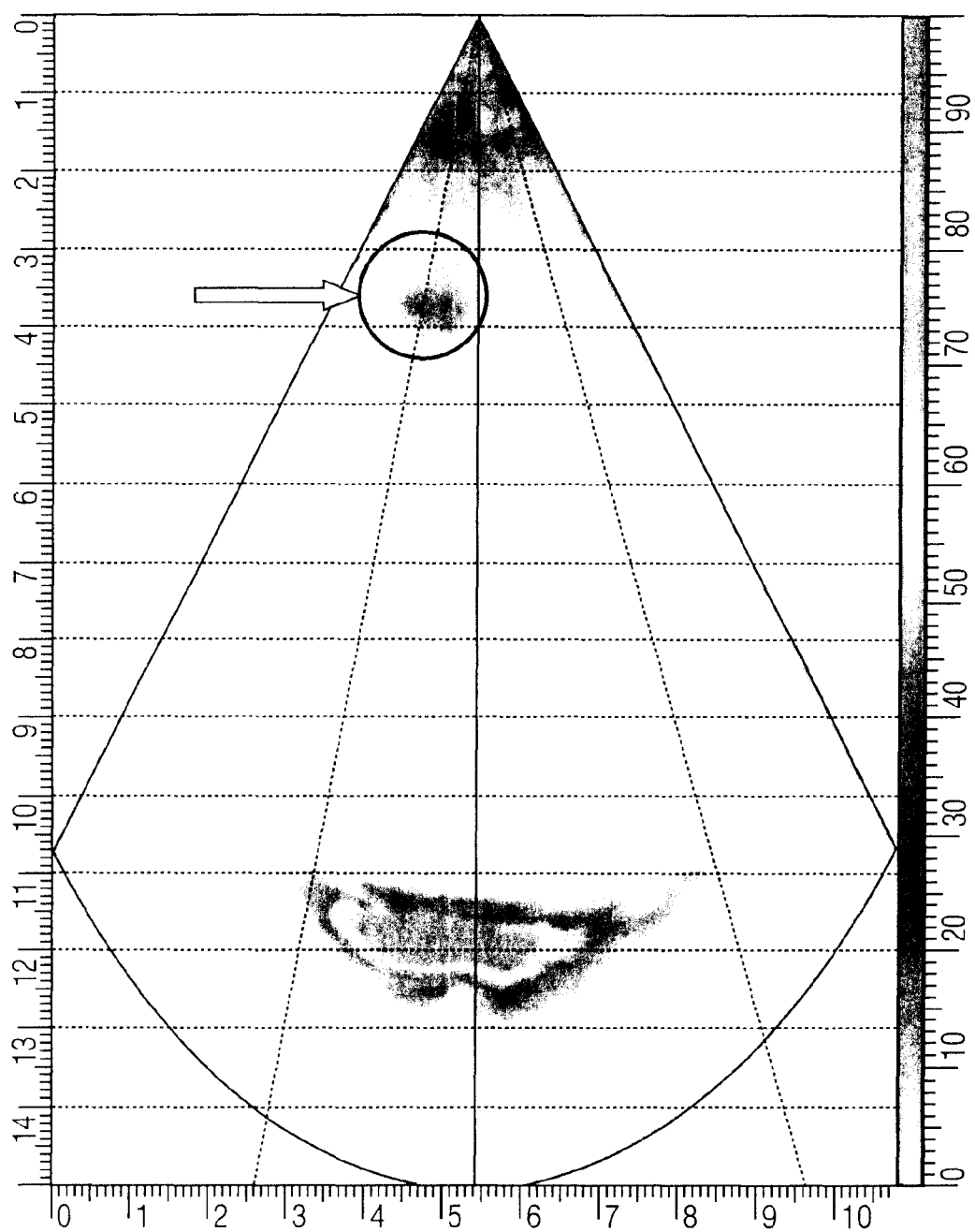

FIGS. 3a-3c are A, B, and S scans of the monolith of FIGS. 2a and 2b, with a cylindrical defect in the monolith wall. The arrows point to the portions of the scans which alert the operator of the defect, or are identified automatically by software implementation.

The procedure for scanning a single monolith can be implemented by several methods. The methods include rotating the monolith while scanning it from a single face, rotating the transducer 360° in a circular pattern around the monolith or in another predefined path, or using multiple transducers on one side to encompass more of the monolith and reduce and possibly eliminate the need for movement altogether. All of these methods will enable the monolith to be analyzed efficiently with minimal time consumption from a single face. The ability to encompass a sweeping (moveable scanning and recording) mode of scanning will cover a broader view of the entire monolith.

The moveable scan (sweep scan) will cover more of the entire volume of the filter and potentially eliminate the need for removing the filter from the assembly process. This device has functionality to reduce the amount of time spent analyzing individual filters, while providing a more detailed description of any flaw detected. Filters can now be scanned online, images can detect flaws with defined criteria as configured within the gate settings, while eliminating an operator.

The above settings have made it possible to detect a 0.0625"×0.250" hole within a filter at a distance of approximately 3.5 in. from the outlet face of a DPF/CDPF, the hole extending radially from the side wall of the DPF/CDPF. This flaw was created within the filter by puncturing through the skin and penetrating the side wall. This type of flaw is cylindrical in nature and potentially the most difficult type of flaw to detect, as ideally, sound requires a parallel face to reflect back to the transducer. This flaw is also more difficult to detect due to its placement near the skin. This flaw was also detected even after "repairing" the flaw with cordierite cement.

It has not been possible to detect such flaws previously by ultrasonic methods. It should be noted that not only was the flaw relatively small and of a shape which is difficult to deflect, it also was located 3.5 inches from the outlet face, i.e. some 8.5 inches from the front face where the transducer is located.

Upon location of a flaw, the monolith may be repaired, for example with cordierite cement if repair is possible, or may be removed and disposed of. It is foreseen that the procedure will become automated, and that the monoliths will be manufactured with an index mark of some type so that the defects occurring in each individual monolith may be incorporated into a database and analyzed. Through such a procedure, for example, it may be noted that certain defects tend to occur somewhat regularly in a given area of the monolith. The production process can then be scrutinized in an effort to try to determine and correct the source of these defects. The defects may indicate that a slight redesign of monolith channels, channel size, wall thickness, etc., may be necessary.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for the detection of flaws in internal combustion engine exhaust system ceramic monoliths, comprising:
    close coupling an ultrasonic transducer to an inlet face or outlet face of a ceramic monolith to be tested;
    scanning the monolith by transmitting ultrasound into the monolith to a predetermined depth which is at least half the depth of the monolith as measured from the inlet face to the outlet face, and if the depth of the scan is less than the depth of the monolith, repeating the scan from the opposite face;
    analyzing reflected ultrasound for the presence of flaws in the monolith, wherein ultrasound emitted by the transducer emanates at an angle to a normal to the face of the monolith.

2. The process of claim 1, wherein close coupling is achieved by inserting an elastomeric sheet against the face of the monolith and between the transducer and the monolith and pressing the transducer against the elastomeric sheet.

3. The process of claim 1, wherein a gel, grease, or viscous liquid is applied between the transducer and the elastomeric sheet.

4. The process of claim 1, wherein the transducer and the monolith move relative to each other.

5. The process of claim 4, wherein the transducer is stationary, and the monolith rotates around an axis located in a face of the monolith and parallel to its length.

6. The process of claim 1, wherein a first scan is made at one rotational position of the monolith and the transducer, and a second scan is made at a second rotational position.

7. The process of claim 6, wherein the second rotational position is 180° from the first rotational position.

8. The process of claim 4, wherein the monolith is stationary and the transducer is rotated around the face of the monolith.

9. The process of claim 1, wherein the transducer comprises an array of a plurality of individual ultrasound-generating elements.

10. The process of claim 1, wherein the reflected sound is analyzed into a plurality of different scan types, and the scans of the plurality of scan types, and the scans of the plurality of scan types are compared to confirm the presence or absence of a defect.

11. The process of claim 10, wherein an A-scan, B-scan, and S-scan are the plurality of scan types.

12. The process of claim 1, further comprising providing an index indicia on the monolith at the time of its manufacture such that defects can be correlated in location relative to the index mark.

13. The process of claim 12, further comprising collecting a database of flaw locations and analyzing the database for statistically significant clusters of flaws.

14. The process of claim 1, wherein the monolith is a diesel particulate filter, optionally coated.

15. The process of claim 1, wherein the ultrasonic transducer is a phased array transducer, and the radiation pattern of the transducer is altered relative to the position of the transducer by altering the phase of electromagnetic energy applied to individual ultrasonic emitting elements within the transducer.

16. A method for the detection of flaws in internal combustion engine exhaust system ceramic monoliths, comprising:
    close coupling an ultrasonic transducer to an inlet face or outlet face of a ceramic monolith to be tested;
    scanning the monolith by transmitting ultrasound into the monolith to a predetermined depth which is at least half the depth of the monolith as measured from the inlet face to the outlet face, and if the depth of the scan is less than the depth of the monolith, repeating the scan from the opposite face;
    analyzing reflected ultrasound for the presence of flaws in the monolith, wherein the reflected sound is analyzed into a plurality of different scan types, and the scans of the plurality of scan types are compared to confirm the presence or absence of a defect and wherein the plurality of scan types are an A-scan, B-scan, and S-scan.

17. The process of one of claim 16, wherein close coupling is achieved by inserting an elastomeric sheet against the face of the monolith and between the transducer and the monolith and pressing the transducer against the elastomeric sheet.

18. The process of one of claim 16, wherein a gel, grease, or viscous liquid is applied between the transducer and the elastomeric sheet.

19. The process of claim 16, wherein the transducer and the monolith move relative to each other.

20. The process of claim 19, wherein the transducer is stationary, and the monolith rotates around an axis located in a face of the monolith and parallel to its length.

21. The process of claim 16, wherein a first scan is made at one rotational position of the monolith and the transducer, and a second scan is made at a second rotational position.

22. The process of claim 21, wherein the second rotational position is 180° from the first rotational position.

23. The process of claim 19, wherein the monolith is stationary and the transducer is rotated around the face of the monolith.

24. The process of claim 16, wherein the transducer comprises an array of a plurality of individual ultrasound-generating elements.

25. The process of claim 16, further comprising providing an index indicia on the monolith at the time of its manufacture such that defects can be correlated in location relative to the index mark.

26. The process of claim 25, further comprising collecting a database of flaw locations and analyzing the database for statistically significant clusters of flaws.

27. The process of claim 16, wherein the monolith is a diesel particulate filter, optionally coated.

28. The process of claim 16, wherein the ultrasonic transducer is a phased array transducer, and the radiation pattern of the transducer is altered relative to the position of the transducer by altering the phase of electromagnetic energy applied to individual ultrasonic emitting elements within the transducer.

29. A method for the detection of flaws in internal combustion engine exhaust system ceramic monoliths, comprising:
    close coupling an ultrasonic transducer to an inlet face or outlet face of a ceramic monolith to be tested;
    scanning the monolith by transmitting ultrasound into the monolith to a predetermined depth which is at least half the depth of the monolith as measured from the inlet face to the outlet face, and if the depth of the scan is less than the depth of the monolith, repeating the scan from the opposite face;
    analyzing reflected ultrasound for the presence of flaws in the monolith, wherein an index indicia on the monolith at the time of its manufacture is provided such that defects can be correlated in location relative to the index mark.

30. The process of one of claim 29, wherein close coupling is achieved by inserting an elastomeric sheet against the face of the monolith and between the transducer and the monolith and pressing the transducer against the elastomeric sheet.

31. The process of claim 29, wherein a gel, grease, or viscous liquid is applied between the transducer and the elastomeric sheet.

32. The process of claim 29, wherein the transducer and the monolith move relative to each other.

33. The process of claim 32, wherein the transducer is stationary, and the monolith rotates around an axis located in a face of the monolith and parallel to its length.

34. The process of claim 29, wherein a first scan is made at one rotational position of the monolith and the transducer, and a second scan is made at a second rotational position.

35. The process of claim 34, wherein the second rotational position is 180° from the first rotational position.

36. The process of claim 29, wherein the monolith is stationary and the transducer is rotated around the face of the monolith.

37. The process of claim 29, wherein the transducer comprises an array of a plurality of individual ultrasound-generating elements.

38. The process of claim 29, wherein the reflected sound is analyzed into a plurality of different scan types, and the scans of the plurality of scan types, and the scans of a plurality of scan types are compared to confirm the presence or absence of a defect.

39. The process of claim 29, further comprising collecting a database of flaw locations and analyzing the database for statistically significant clusters of flaws.

40. The process of claim 29, wherein the monolith is a diesel particulate filter, optionally coated.

41. The process of claim 29, wherein the ultrasonic transducer is a phased array transducer, and the radiation pattern of the transducer is altered relative to the position of the transducer by altering the phase of electromagnetic energy applied to individual ultrasonic emitting elements within the transducer.

* * * * *